United States Patent
Staub et al.

(10) Patent No.: US 6,849,778 B1
(45) Date of Patent: Feb. 1, 2005

(54) METHODS AND VECTORS FOR SITE-SPECIFIC RECOMBINATION IN PLANT CELL PLASTIDS

(75) Inventors: Jeffrey M. Staub, Chesterfield, MO (US); Peter H. J. Hajdukiewicz, Chesterfield, MO (US); Larry Gilbertson, Chesterfield, MO (US)

(73) Assignee: Calgene LLC, Davis, CA (US)

(*) Notice: Subject to any disclaimer, the term of this patent is extended or adjusted under 35 U.S.C. 154(b) by 0 days.

(21) Appl. No.: 09/688,851

(22) Filed: Oct. 16, 2000

Related U.S. Application Data
(60) Provisional application No. 60/225,542, filed on Aug. 16, 2000, and provisional application No. 60/159,876, filed on Oct. 15, 1999.

(51) Int. Cl.[7] .................. A01H 1/00; C12N 15/82; C12N 15/74; C12N 15/87; C07H 21/04
(52) U.S. Cl. .................. 800/278; 800/298; 800/300; 800/317.3; 435/320.1; 435/419; 536/23.1
(58) Field of Search ............... 536/23.1; 435/320.1, 435/419, 183, 468; 800/278, 298, 300, 317.3, 294

(56) References Cited

FOREIGN PATENT DOCUMENTS
| WO | WO 97/41228 A2 | 11/1997 |
| WO | WO 01/21768 A1 | 3/2001 |

OTHER PUBLICATIONS

Birch, R.G. Plant Transformation: Problems and Strategies for Practical Application; Annu Rev. Plant Physiol. Plant Mol. Biol. 1997, 48:297–326.*

Odell et al; Use of site–specific recombination systems in plants; 1994. In J Paszkowski, Ed, Homologous Recombination in Plants. Kluewer Academic Publishers, Dordrecht, The Netherlands, pps 219–270.*

Kilby, et al, 1993, Trends in Genetics 9: 413–421.*

Svab, et al, (Proc. Natl. Acad. Sci. USA, vol. 90, pp. 913–917, 1993).*

Dale, et al, (Proc. Natl. Acad. Sci. USA, vol. 88, pp. 10558–10562, 1991.*

Dale E.C. et al, "Gene transfer with subsequent removal of the selection gene from the host genome," PNAS USA, National Academy of Science (Washington), p. 10558–62, (Dec. 1991).

Dale E.C. et al, "Intra– and intermolecular site–specific recombination in plant cells mediated by bacteriophage P1 recombinase," Gene, Elsevier (Amsterdam), 9: p. 79–85, (1990).

* cited by examiner

Primary Examiner—Phuong T. Bui
Assistant Examiner—Georgia Helmer
(74) Attorney, Agent, or Firm—M. Todd Rands

(57) ABSTRACT

Novel compositions and methods useful for genetic engineering of plant cells are provided. In particular, plastid constructs comprising recombining sites are provided. Such constructs find use in methods for site specific recombination in plant cell plastids. Plant cells and plants comprising the constructs described herein, as well as plant cells and plants produced by the methods of the present invention are of interest.

4 Claims, 8 Drawing Sheets

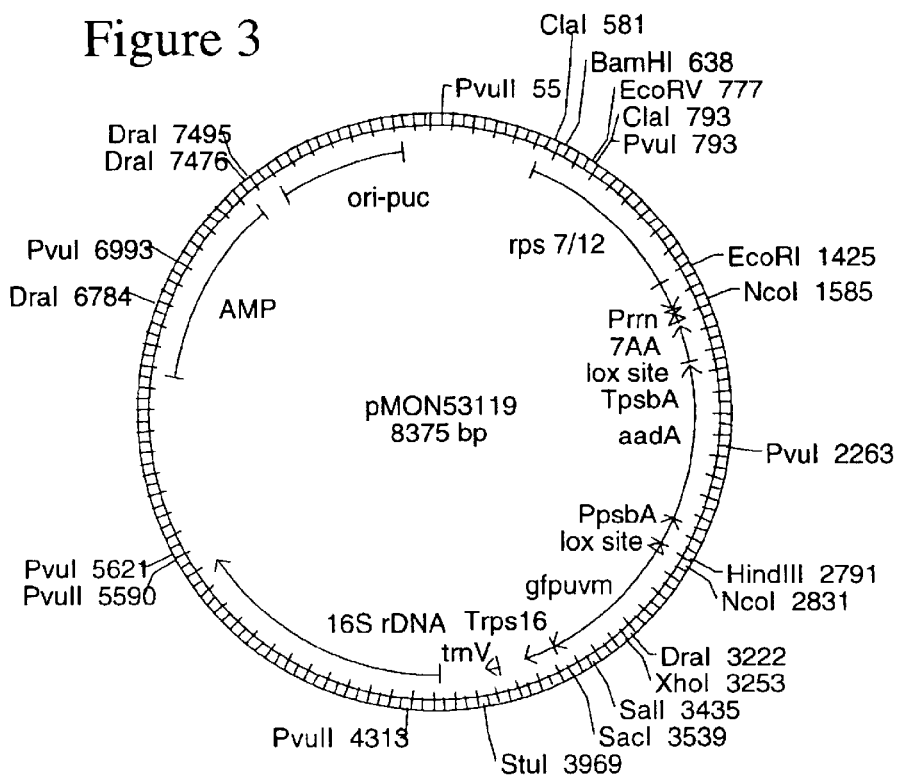
Figure 3
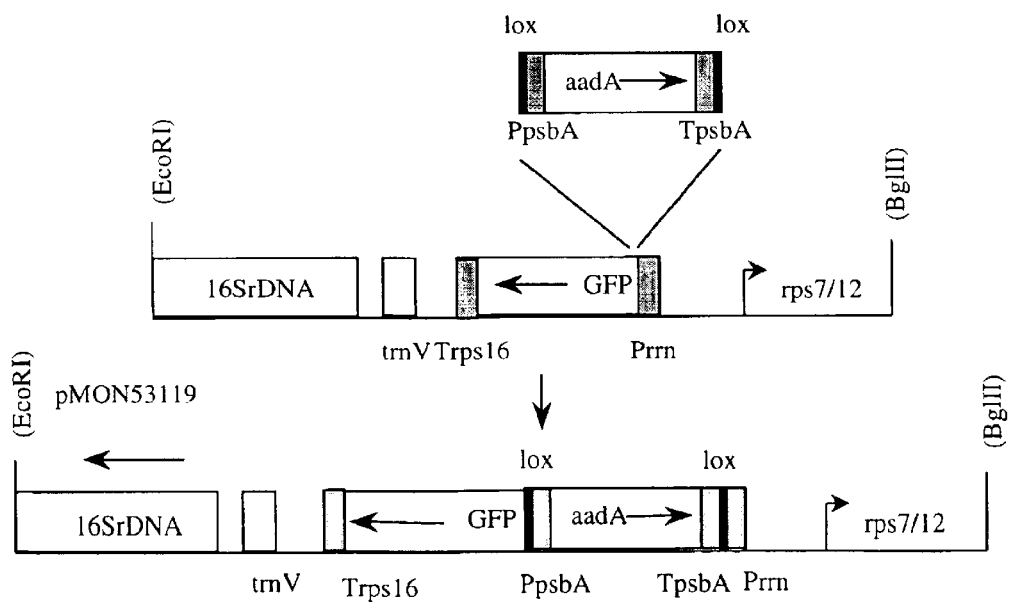

Alternate Excision (a) - Nt-Act2-53119-38

Alternate Excision - Clone Nt-35S-53119-2

SEQUENCE LISTING

```
<160> NUMBER OF SEQ ID NOS: 5

<210> SEQ ID NO 1
<211> LENGTH: 34
<212> TYPE: DNA
<213> ORGANISM: Bacteriophage P1

<400> SEQUENCE: 1
ataacttcgt atagcataca ttatacgaag ttat                              34

<210> SEQ ID NO 2
<211> LENGTH: 32
<212> TYPE: DNA
<213> ORGANISM: Artificial Sequence
<220> FEATURE:
<221> NAME/KEY: misc_feature
<223> OTHER INFORMATION: synthetic construct

<400> SEQUENCE: 2
gggcatgccg ccagcgttca tcctgagcca gg                                32

<210> SEQ ID NO 3
<211> LENGTH: 37
<212> TYPE: DNA
<213> ORGANISM: Artificial Sequence
<220> FEATURE:
<221> NAME/KEY: misc_feature
<223> OTHER INFORMATION: synthetic construct

<400> SEQUENCE: 3
ggggatccca aattgacggg ttagtgtgag cttatcc                           37

<210> SEQ ID NO 4
<211> LENGTH: 35
<212> TYPE: DNA
<213> ORGANISM: Nicotiana tabacum

<400> SEQUENCE: 4
ctattatatt agattagtat tagttagtga tcccg                             35

<210> SEQ ID NO 5
<211> LENGTH: 37
<212> TYPE: DNA
<213> ORGANISM: Artificial Sequence
<220> FEATURE:
```

```
-continued

<221> NAME/KEY: misc_feature
<223> OTHER INFORMATION: recombination junction of loxP site

<400> SEQUENCE: 5
ctattatatt agattagtgt atgctatacg aagttat                                      37
```

METHODS AND VECTORS FOR SITE-SPECIFIC RECOMBINATION IN PLANT CELL PLASTIDS

This application claims priority to U.S. provisional application 60/159,876 filed Oct. 15, 1999 and 60/225,542 filed Aug. 16, 2000, herein incorporated by reference in their entirety.

INTRODUCTION

Technical Field

This invention relates to the application of genetic engineering techniques to plants. More specifically, the invention relates to constructs and methods for use of site specific recombination systems for the production of plastid transformed plants.

Background

Molecular biological techniques have enabled researchers to introduce pieces of DNA from one organism to another organism. Such techniques, referred to as recombinant DNA technology, have positively impacted the areas of medicine and agriculture. Conventional cloning methods have enabled the introduction of new pharmaceuticals and improved crops of agricultural importance. As the need for the introduction of multiple pieces of DNA and larger fragments of DNA into various target hosts increases, the need for novel cloning strategies increases accordingly.

The plastids of higher plants are an attractive target for genetic engineering. Plant plastids (chloroplasts, amyloplasts, elaioplasts, chromoplasts, etc.) are the major biosynthetic centers that in addition to photosynthesis are responsible for production of industrially important compounds such as amino acids, complex carbohydrates, fatty acids, and pigments. Plastids are derived from a common precursor known as a proplastid and thus the plastids present in a given plant species all have the same genetic content. Plant cells contain 500–10,000 copies of a small 120–160 kilobase circular genome, each molecule of which has a large (approximately 25 kb) inverted repeat. Thus, it is possible to engineer plant cells to contain up to 20,000 copies of a particular gene of interest, which potentially can result in very high levels of foreign gene expression.

Previous studies directed to stable transformation of plant chloroplasts have relied on homologous recombination to incorporate desired gene constructs into plastids using a selectable marker for selection of transplastomic plants. In this manner, transgenic plants homoplastic, or near-homoplastic, for a recombinant DNA construct may be obtained. However, at present, methods for multiple rounds of plastid transformation (for example for gene stacking) are restricted due to the limited number of selectable markers described for plastid transformation. Thus, there is a need in the art for constructs and methods for performing multiple rounds of plastid transformation. This is done by removing the selectable marker gene after each round of transformation by site-specific recombination.

SUMMARY OF THE INVENTION

By this invention, constructs and methods for genetic engineering of plant cells to provide for site-specific recombination of foreign DNA sequences inserted into the plant plastid are provided.

In a first aspect of the present invention recombinant nucleic acid constructs are provided that are useful for site-specific recombination of nucleic acid sequences in a plant cell plastid. In particular, plastid constructs are provided that comprise at least one DNA sequence, and at least two recombining sites. Particularly preferred constructs are those that employ Lox recombining sites.

Another aspect of the present invention provides recombinant nucleic acid constructs having two DNA sequences with the recombining sites positioned between the DNA sequences.

A further aspect of the present invention provides recombinant nucleic acid constructs having a DNA sequence positioned between the recombining sites.

Another aspect of the present invention are recombinant nucleic acid constructs comprising a transcription initiation region functional in a plant cell, an organelle targeting sequence, and a nucleic acid sequence encoding recombinase. Such constructs are referred to herein as recombinase constructs.

The recombinase constructs of the present invention provide for expressing a recombinase in host plant cell tissues. Such constructs include plastid constructs and nuclear constructs. Nuclear constructs include those that provide for constitutive expression of the recombinase in all plant cells and those that provide for expression preferentially in particular plant tissues and/or at particular developmental stages.

Also considered part of the present invention are the plants and plant cells comprising the constructs of the present invention.

Another aspect of the present invention is to provide methods for directing site-specific recombination in a host plant cell plastid. In particular, host plant cells are transformed or transfected with the plastid constructs having at least one DNA sequence and at least two recombining sites. The method further comprises providing a recombinase into the plant cell.

In a further aspect, the present invention relates to methods of retransforming a plant cell plastid using the same selectable marker.

Also considered in the present invention are the plant cells and plants produced by the methods described herein.

DESCRIPTION OF THE FIGURES

FIG. 1 also shows the loxP target sequence that comprises two 13-base pair (bp) inverted repeats, and a central or core 8-bp sequence referred to as the "spacer region."

FIG. 3 provides a schematic diagram of the plastid construct pMON53119.

DETAILED DESCRIPTION OF THE INVENTION

Figure 1:
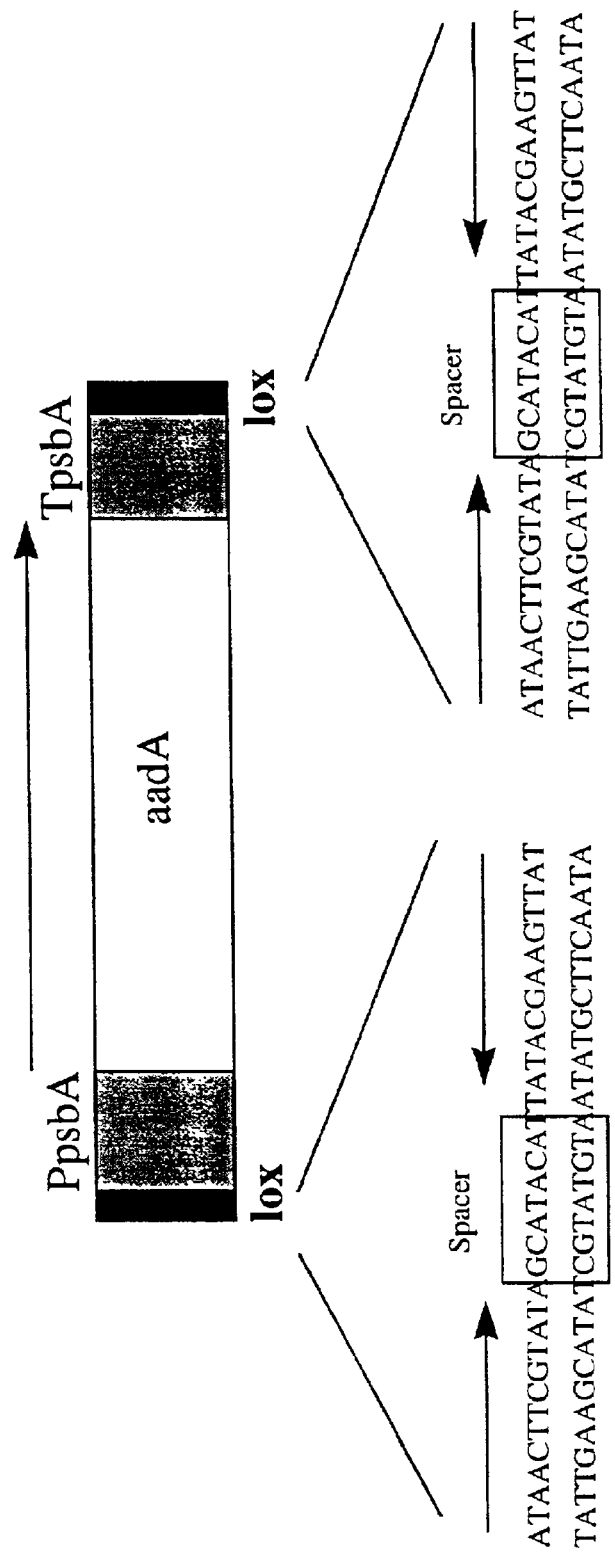
FIG. 1 provides the aadA plastid expression cassette positioned between two loxP recombining sites.

In accordance with the subject invention, constructs and methods are provided for site-specific recombination of introduced nucleic acid sequences in host plant cell plastids. The methods of the present invention provide a novel means for obtaining transplastomic plants.

As used herein, transplastomic refers to a plant cell having an introduced nucleic acid, where the introduced nucleic acid is introduced into the plant cell plastid. The introduced nucleic acid may be integrated into the plastid genome or may be contained in an autonomously replicating plasmid. Preferably, the nucleic acid is integrated into the genome of the plant cell plastid.

The term "introduced" in the context of inserting a nucleic acid sequence into a cell means "transfection" or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

In one embodiment of the present invention, constructs are provided that allow for the site-specific recombination of a nucleic acid sequence in a host plant cell plastid. Such constructs are referred to herein as plastid expression constructs. In general, the constructs comprise at least one DNA sequence and at least two recombining sites.

As used herein, "recombining sites" (also referred to herein as "recombination sites") refer to nucleic acid sequences comprising inverted palindromes separated by an asymmetric sequence at which a site-specific recombination can occur. Such recombining sites can include, but are not limited to, Lox (Sternberg et al. (1978) *Cold Spring Harbor Symp. Quant. Biol.* 43:1143–1146 and Hoess et al. (1990) In *Nucleic Acids and Molecular Biology*, Eds Eckstein and Lilley (Springer, Berlin), vol 4, pp 99–109) and FRT (reviewed in Kilby et al. (1993) *Trends In Genetics*, 9, 413–421).

Any site-specific recombination system can be used in accordance with the present invention in the plastid expression constructs. More preferably, any similar recombination system in which the recognition site for the recombinase consists of binding sites flanking an asymmetric spacer sequence can be used. Particularly preferred site-specific recombination systems would include, but are not limited to, the Cre/lox and FLP/FRT site-specific recombination systems. Both the Cre recombinase derived from bacteriophage P1 and the FLP recombinase derived from *Saccharomyces cerevisiae* mediate site-specific recombination between a pair of target sequences and are members of the integrase family. The chemical structures of over 100 members of the Int family of site-specific recombinases have been compared (Nunes-Duby et al., Nucl. Acids Res. 26, 2:391–406). The recombination mechanism of these systems has also been investigated (Craig, Annu. Rev. Genet. 22:77–105, 1988; Grindley, Curr. Biol., 7:608–612, 1997).

The loxP recombination site is the target sequence for the Cre recombinase. The loxP target sequence comprises two 13-base pair (bp) inverted repeats and a central or core 8-bp sequence referred to as the "spacer region." The Cre recombinase catalyzes a reversible reaction wherein fragments of DNA in between the wild-type loxP sites can be excised, integrated, or exchanged in a crossover event with another DNA molecule containing a pair of compatible lox sites. A compatible site as used herein means a recombining site that is capable of recombination with another recombining site. Accordingly, two wild-type loxP sites are compatible (capable of recombination with each other). Compatible lox sites can also excise DNA as well as integrate DNA. In this regard, compatible lox sites can be useful for cloning methods in which excision of DNA fragments is desired.

Of interest in the plastid constructs of the present invention is the use of at least two recombining sites. In particular, where two recombining sites are employed, the two sites are preferably compatible. Where more than two recombining sites are employed, for example four recombining sites, the sites will be provided in pairs. The individual recombining sequences of each pair are preferably compatible; however, the sequences of one pair can be compatible with members of a second pair or can be non-compatible (not capable of recombination with each other).

The DNA sequence for use in the plastid constructs of the present invention can be any DNA sequence. DNA sequences of interest for use in the plastid constructs of the present invention include, but are not limited to, blocking sequences and expression constructs.

Blocking sequences refer to nucleic acid sequences that are located between two sequences of interest. Excision of the blocking sequences results in the two sequences being brought into operable association. For example, where the DNA sequence is located between a plastid functional promoter and a nucleic acid sequence to be expressed from the promoter, excision of the blocking sequence results in the promoter and the nucleic acid sequence of interest being brought together to form a functional expression cassette. Such blocking sequences have been described, for example, for use in the nuclear genome in U.S. Pat. No. 5,925,808.

Also of interest for use in the plastid constructs of the present invention is a DNA sequence positioned between two recombining sites. Of particular interest is a DNA sequence comprising a plastid expression cassette. The cassettes preferably have a plastid promoter and a DNA sequence of interest. The recombining sites can be positioned within the expression cassette, outside the expression cassette, or combinations thereof. Of interest in the plastid expression cassettes are nucleic acid sequences encoding genes of interest. Of particular interest is the use of sequences encoding genes that confer resistance to herbicides or antibiotics. Of most particular interest is the use of selectable markers in the plastid expression cassettes.

Where the recombining sites are positioned outside the cassette, the sites can be positioned 5' to the promoter. Positioned 5' to the promoter refers to a recombining site located upstream of the promoter with respect to the direction of transcription. In addition, the recombining sites can be positioned 3' of the DNA sequence of interest. Positioned 3' of the DNA sequence of interest refers to the location of the recombining site downstream of the sequence with respect to the direction of transcription. Such positioning 5' or 3' allows for the placement of additional sequences, such as transcriptional enhancers, transcriptional termination sequences, and the like between the recombining site and the promoter and/or DNA sequence. Furthermore, recombining sites can be positioned as to place the DNA sequence between the recombining sites.

Thus, where a DNA sequence is positioned between two compatible recombining sites, the sequence can be removed by providing a compatible recombinase. A compatible recombinase refers to a recombinase that recognizes a specific recombining sequence.

Also provided in the present invention are recombinase constructs. Such constructs comprise a promoter functional in a plant cell, a plastid targeting sequence, and a nucleic acid sequence encoding a protein involved in recombination between particular recombining sites. Such proteins are referred to as recombinases.

Nucleic acid sequences encoding recombinases for use in the present invention include any recombinase involved in recombination between particular recombining sites. Preferably, the recombinase used in the constructs of the present invention is functional towards the recombining sites employed in the plastid expression constructs. Most preferred in the present invention are the Cre, FLP and R recombinases. Most especially preferred is the Cre recombinase.

The Cre, FLP and R recombinases belong to the lambda integrase family of DNA recombinases (reviewed in Kilby et al. (1993) *Trends in Genetics*, 9:413–421; Landy (1993) *Current Opinion in Genetics and Development*, 3:699–707; Argos et al. (1986) EMBO J., 5:433–440). The Cre and FLP recombinases show similarities, both in terms of the types of reactions they carry out and in the structure of their target sites and mechanism of recombination (see, e.g., Jayaram (1994) *Trends in Biological Sciences*, 19:78–82; Lee et al. (1995) *J. Biolog. Chem.*, 270:4042–4052; Whang et al. (1994) *Molec. Cell. Biolog.*, 14:7492–7498; Lee et al. (1994) EMBO J., 13:5346–5354; Abremski et al. (1986) *J. Mol. Biol.*, 192:17–26; Adams et al. (1992) *J. Mol. Biol.*, 226:661–673). For instance, the recombination event is independent of replication and exogenous energy sources such as ATP and functions on both supercoiled and linear DNA templates.

The Cre and FLP recombinases exert their effects by promoting recombination between two of their target recombination sites, Lox and Frt, respectively. Both target sites are comprised of inverted palindromes separated by an asymmetric sequence (see, e.g., Mack et al. (1992) *Nucleic Acids Research*, 20:4451–4455; Hoess et al. (1986) *Nucleic Acids Research*, 14:2287–2300; Kilby et al.(1993) supra). The asymmetry provides directionality to the recombination event. Namely, recombination between target sites arranged in parallel (also referred to as "direct repeats") on the same linear DNA molecule results in excision of the intervening DNA sequence (the DNA sequence that is flanked by the recombining sites) as a circular molecule (Kilby et al. (1993) supra). Recombination between direct repeats on a circular DNA molecule excises the intervening DNA and generates two circular molecules. In comparison, recombination between antiparallel sites (sites that are in opposite orientation, also referred to as "inverted repeats") on a linear or circular DNA molecule results in inversion of the internal sequence. Even though recombinase action can result in reciprocal exchange of regions distal to the target site when targets are present on separate linear molecules, intramolecular recombination is favored over intermolecular recombination.

Any nucleic acid can be introduced into a host cell plastid by the methods encompassed by the present invention including, for example, DNA sequences or genes from another species, and/or genes or sequences that originate with or are present in the same species but are incorporated into recipient cells by genetic engineering methods rather than classical reproduction or breeding techniques. An introduced piece of DNA can be referred to as exogenous DNA. Exogenous as used herein is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The constructs of the present invention find use in methods for site-specific recombination in host plant cell plastids.

The methods of the present invention involve introducing plastid constructs described herein into a plant cell plastid and providing the cell with a recombinase. The recombinase can be provided to the transplastomic plant cell by a variety of methods including, but not limited to, expressing the recombinase in a plant cell nucleus and targeting the expressed gene to the plastid, expressing the recombinase from the plant cell plastid, various culture conditions, sprays, and the like.

Of particular interest in the methods of the present invention is the use of nucleotide sequences encoding recombinases in recombinant DNA constructs to direct expression of the recombinase protein to a host cell plastid. Of particular interest is the use of the polynucleotide sequences encoding recombinase in recombinant DNA constructs employing a plastid targeting sequence to direct the expressed recombinase to the host plant cell plastid.

The recombinase expression constructs generally comprise a promoter (also referred to as a transcriptional initiation region) functional in a plant host cell operably linked to a nucleic acid sequence encoding a recombinase having a plastid targeting sequence and a transcriptional termination region functional in a host plant cell.

Those skilled in the art will recognize that there are a number of promoters that are functional in plant cells and have been described in the literature. Chloroplast and plastid specific promoters, chloroplast or plastid functional promoters, and chloroplast or plastid operable promoters are also envisioned.

Any plant promoter can be used as a 5' regulatory sequence for modulation of expression of a particular gene or genes. The promoter region contains a sequence of bases that signals RNA polymerase to associate with the DNA and to initiate the transcription into mRNA using one of the DNA strands as a template to make a corresponding complementary strand of RNA. Those of skill in the art are aware of the numerous types of promoters that can be used in a plant expression vector and a number of promoters that are active in plant cells have been described in the literature. A number of promoters have utility for plant gene expression for any gene of interest including, but not limited to, selectable markers, scorable markers, genes for pest tolerance, disease tolerance, nutritional enhancements and any other gene of agronomic interest. Examples of constitutive promoters useful for plant gene expression include, but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988) and the octopine synthase promoter (Fromm et al., Plant Cell 1:977, 1989); and the figwort mosaic virus (FMV) promoter. Other types of promoters are also envisioned to have utility in the present invention including, but not limited to, tissue-enhanced promoters, developmentally regulated promoters, or inducible promoters.

Of interest in the present invention are promoters that are functional during zygote formation (before seeds germinate) or subsequent seedling germination. Examples of such promoters include, but are not limited to, Act2 and Act8 (An et al. (1996) *Plant J.*, 10:107–121) and Perl (Haslekas (1998) *Plant Mol Biol* 36(6):833–45).

Preferably, the proteins conferring various recombinases are directed to a particular subcellular compartment, for example, to the mitochondrion, endoplasmic reticulum, vacuoles, chloroplast or other plastidic compartment. For example, where the recombinase will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481.

Regulatory transcript termination regions may be provided in plant expression constructs of this invention as well. Transcript termination regions may be provided by any convenient transcription termination region derived from a gene source, for example, the transcript termination region that is naturally associated with the transcript initiation region. The skilled artisan will recognize that any convenient transcript termination region that is capable of terminating transcription in a plant cell may be employed in the constructs of the present invention.

Alternatively, constructs may be prepared to direct the expression of the recombinase sequences directly from the host plant cell plastid. Such constructs and methods are known in the art and are generally described, for example, in Svab et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a nucleic acid sequence.

The constructs of the present invention can be employed with a wide variety of plant life. Plants of interest include, but are not limited to, rapeseed (Canola and High Erucic Acid varieties), sunflower, safflower, *Arabidopsis*, rice, cotton, soybean, peanut, coconut and oil palms, wheat, and corn. Depending on the method for introducing the recombinant constructs into the host cell, other DNA sequences may be required. Importantly, this invention is applicable to dicotyledonous and monocotyledonous species alike and will be readily applicable to new and/or improved transformation and regulation techniques.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to *Agrobacterium* infection may be successfully transformed via tripartite or binary vector methods of *Agrobacterium*-mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed that allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g., antibiotic, heavy metal, toxin, etc.; complementation providing prototrophy to an auxotrophic host; viral immunity or the like. Depending upon the number of different host species the expression construct or components thereof are introduced into, one or more markers may be employed, where different conditions for selection are used for the different hosts.

Where *Agrobacterium* is used for plant cell transformation, a vector may be used that may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region (s) will be inserted into a broad host range vector capable of replication in *E. coli* and *Agrobacterium*, there being broad host range vectors described in the literature. Commonly used is pRK2 or derivatives thereof. See, for example, Ditta et al. (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (*Plant Mol. Biol.* (1990) 14:269–276), wherein the pRiHRI (Jouanin et al., *Mol. Gen. Genet.* (1985) 201:370–374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants.

The plants may then be grown to seed and the seed used to establish repetitive generations and for isolation of vegetable oils.

In order to provide a means of selecting the desired plant cells following plastid transformation, the polynucleotides for plastid transformation will also contain a construct that provides for expression of a marker gene. Expression of the marker gene product allows for selection of plant cells comprising plastid organelles that are expressing the marker protein. In the examples provided herein, a bacterial aadA gene is expressed under the regulatory control of chloroplast 5' promoter and 3' transcription termination regions. The use of such an expression construct for plastid transformation of plant cells has been described by Svab and Maliga (1993, supra). Expression of the aadA gene confers resistance to spectinomycin and streptomycin and thus allows for the identification of plant cells expressing this marker gene. Selection for the aadA marker gene is based on identification of plant cells that are not bleached by the presence of streptomycin, or more preferably spectinomycin, in the plant growth medium. Other genes that encode a product involved in chloroplast metabolism may also be used as selectable markers. For example, genes that provide resistance to plant herbicides such as glyphosate, bromoxynil or imidazolinone may find particular use. Such genes have been reported by Stalker et al. (*J. Biol. Chem.* (1985) 260:4724–4728; glyphosate resistant EPSP), Stalker et al. (*J. Biol. Chem.* (1985) 263:6310–6314; bromoxynil resistant nitrilase gene), and Sathasivan et al. (*Nucl. Acids Res.* (1990) 18:2188; AHAS imidazolinone resistance gene).

In the examples described herein, the aadA gene is under the control of a tobacco psbA gene promoter, PpsbA. Numerous additional promoter regions may also be used to drive expression of the selectable marker gene, including various plastid promoters, viral and bacterial promoters that have been shown to function in plant plastids.

The polynucleotides for use in plastid transformation will also contain a means of providing for stable transfer of the expression construct and the selectable marker construct into the plastid genome. Conveniently, regions of homology to the target plastid genome flank the constructs to be transferred and provide for transfer to the plastid genome by homologous recombination via a double crossover into the genome. Where the regions of homology are present in the inverted repeat regions (IRA and IRB) of the plastid genome, two copies of the transgene are expected per plastid genome. Typically, the regions of homology with the plastid genome will be approximately 1 kb in size. Smaller regions of homology may also be used, for example as little as 100 bp can provide for homologous recombination into the plastid genome. However, the frequency of recombination and thus the frequency of obtaining plants having transformed plastids may decrease with decreasing size of the homology regions. Example of constructs comprising such regions of homology for tobacco plastid transformation are described in Svab et al. (1990 supra) and Svab and Maliga (1993 supra). Regions useful for recombination into tobacco plastid genomes are also described in the following examples. Similar homologous recombination and selection constructs may be prepared using plastid DNA from the target plant species.

In developing the constructs of the instant invention, the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA that is employed in the regulatory regions, the recombinase encoding sequence and/or the DNA sequences of interest for expression in the plastids. Methods for restriction digests, Klenow blunt end treatments, ligations, and the like are well known to those in the art and are described, for example, by Maniatis et al. (in *Molecular cloning: a laboratory manual* (1982) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation by joining or removing of sequences, linkers, or the like. Normally, the vectors will be capable of replication in at least a relatively high copy number in *E. coli*. A number of vectors are readily available for cloning, including such vectors as pBR322, pUC series, M13 series, and pBluescript (Strategene; La Jolla, Calif.).

Stable transformation of tobacco plastid genomes by particle bombardment has been reported (Svab et al. (1990) *Proc. Natl. Acad. Sci. USA* 87:8526–8530; Svab and Maliga (1993) *Proc. Natl. Acad. Sci. USA* 90:913–917). The methods described in the above references may be employed to obtain plants transformed with the plastid transformation constructs described herein. Briefly, such methods involve DNA bombardment of a target host explant, preferably from a tissue that is rich in metabolically active plastid organelles, such as green plant tissues, including leaves, and cotyledons. The bombarded tissue is then cultured for ~2 days on a cell division promoting media. The plant tissue is then transferred to a selective media containing an inhibitory amount of the particular selective agent, as well as the particular hormones and other substances necessary to obtain regeneration for that particular plant species. For example, in the above publications and the examples provided herein, the selective marker is the bacterial aadA gene and the selective agent is spectinomycin. The aadA gene product allows for continued growth and greening of cells whose chloroplasts comprise the marker gene product. Cells that do not contain the marker gene product are bleached. The bombarded explants will form green shoots in approximately 3–8 weeks. Leaves from these shoots are then subcultured on the same selective media to ensure production and selection of homoplasmic shoots. As an alternative to a second round of shoot formation, the initial selected shoots may be grown to mature plants and segregation relied upon to provide transformed plants homoplastic for the inserted gene construct.

The transformed plants so selected may then be analyzed to determine whether the entire plastid content of the plant has been transformed (homoplastic transformants). Typically, following two rounds of shoot formation and spectinomycin selection, approximately 50% of the transgenic plantlets analyzed are homoplastic as determined by Southern blot analysis of plastid DNA. These plantlets are selected for further cultivation, both for analysis of the transgenic plastid phenotype, or for use in methods to re-transform the transplastomic plants with the recombinase construct.

The constructs of the present invention provide a novel means for the production of plants having transformed plastids. The constructs provide methods for the introduction of polynucleotides into a plant cell plastid. In this manner, transplastomic plants can be obtained in which a particular plastid expression cassette has been removed by the action of the expressed recombinase on the recombining sites. For example, when the plastid expression cassette flanked by the recombining sites contains a selectable marker, the resulting plants can then be used in subsequent rounds of plastid transformation using the same marker for selection of transplastomic plants.

Thus, the present invention provides methods for the production of transplastomic plants. The methods involve the production of plants having an introduced polynucleotide that is removed when contacted with an appropriate recombinase. In general, the polynucleotides for use in the methods will be flanked by recombining sites that are in a parallel orientation.

The invention now being generally described, it will be more readily understood by reference to the following examples, which are included for purposes of illustration only and are not intended to limit the present invention.

EXAMPLES

Example 1

Expression Construct Preparation

Expression constructs are prepared to allow the excision of an introduced marker gene from the plastid genome when expressed in the same plant expressing a recombinase directed to the plastid. The marker gene is flanked by the loxP sequences (5'-ATAACTTCGTAT AGCATACATTATACGAAGTTAT-3' (SEQ ID NO:1), the spacer region is provided as an underline). In addition constructs are prepared to direct the expression of a recombinase from the nuclear genome, and direct the protein to the plastid.

1A. Plastid Expression Constructs

A series of plastid expression constructs are prepared for use in plastid transformations. The constructs are prepared using the aadA selectable marker flanked by directly repeated loxP sites. A schematic diagram of the aadA selectable marker cassette is provided in FIG. 1. FIG. 1 also provides the sequence of the loxP recombining sites. The constructs also employ the use of the Green Fluorescent Protein (GFP) expressed from promoter sequences functional in a plant cell plastid.

The nucleic acid sequence encoding GFP-2 as described by Pang et al. ((1996) Plant Physiol., 112:893–900) was cloned between the Prrn promoter/rbcL ribosome binding site and Trps16 transcription termination sequence. The Prrn promoter with the synthetic ribosome binding site and translationally fused to sequence encoding 7 amino acids of the rbcL coding region is as described in Svab et al. (1993, supra). The Trps16 fragment comprises the rps16 gene 3'-regulatory region from nucleotides 5,087 to 4,939 in the tobacco plastid DNA.

Figure 2:
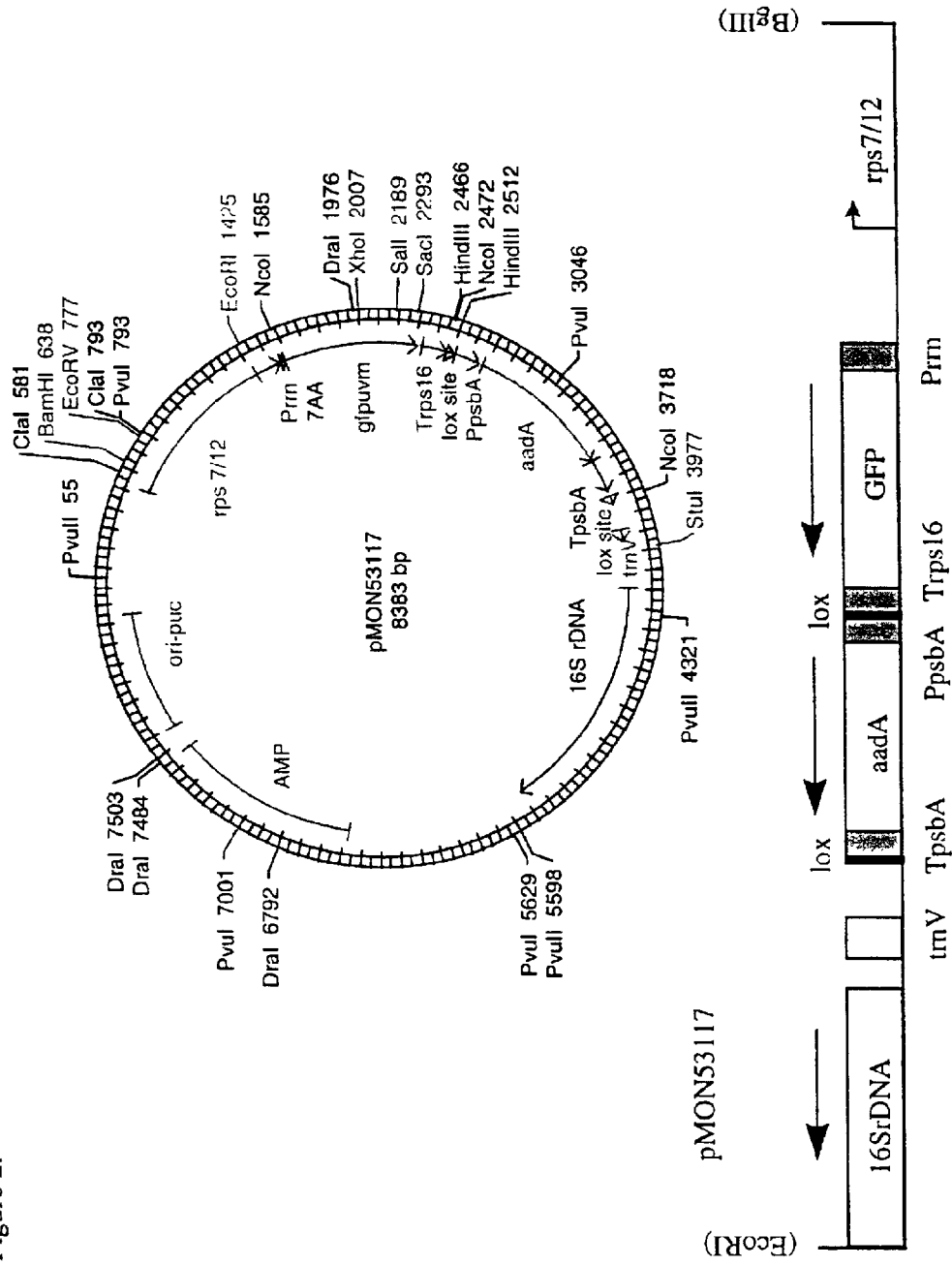
FIG. 2 provides a schematic diagram of the plastid construct pMON53117.

A plastid expression construct, pMON53117 (FIG. 2), was prepared employing the aadA gene under the regulatory control of the psbA promoter and transcriptional terminator. This aadA cassette is flanked by direct repeats of the loxP recombining sites. The expression construct also contains a second cassette containing the GFP sequence under the regulatory control of the rrn promoter and rps16 transcriptional termination region. These two expression cassettes are inserted into the transformation construct pPRV111B (Zoubenko et al. (1994) *Nucleic Acids Research*, 22(19):3819–3824). FIG. 2 provides a schematic diagram of the pMON53117 construct.

A second plastid expression construct, pMON53119 (FIG. 3), was also prepared. This construct is generally the same as described for pMON53117, however, the aadA cassette is cloned between the rrn promoter and the coding sequence of GFP such that expression of the GFP marker gene requires the excision of the aadA cassette by the Cre recombinase. The direction of the aadA cassette is counter to the direction of GFP expression to further ensure that excision of the aadA cassette is necessary for GFP expression. The construct is designed such that excision of the aadA cassette creates a translationally fused lox site in frame with the GFP protein. A schematic diagram of the pMON53119 construct is provided in FIG. 3.

Prior to use in plastid transformation, these constructs were tested in an *E. coli* strain that constitutively expressed the Cre recombinase. Plasmid DNA can be rescued from the transformed *E. coli* and restriction digest analysis can be used to confirm that excision occurred accurately and completely. This analysis confirmed that excision occurred properly for both plastid expression constructs.

1B. Recombinase Constructs

A series of constructs were prepared to direct the expression of the Cre recombinase from the plant cell nucleus and targeted to the plant cell plastid. These constructs employ the use of a plastid transit peptide to direct the recombinase to the plant cell plastid.

Figure 4:
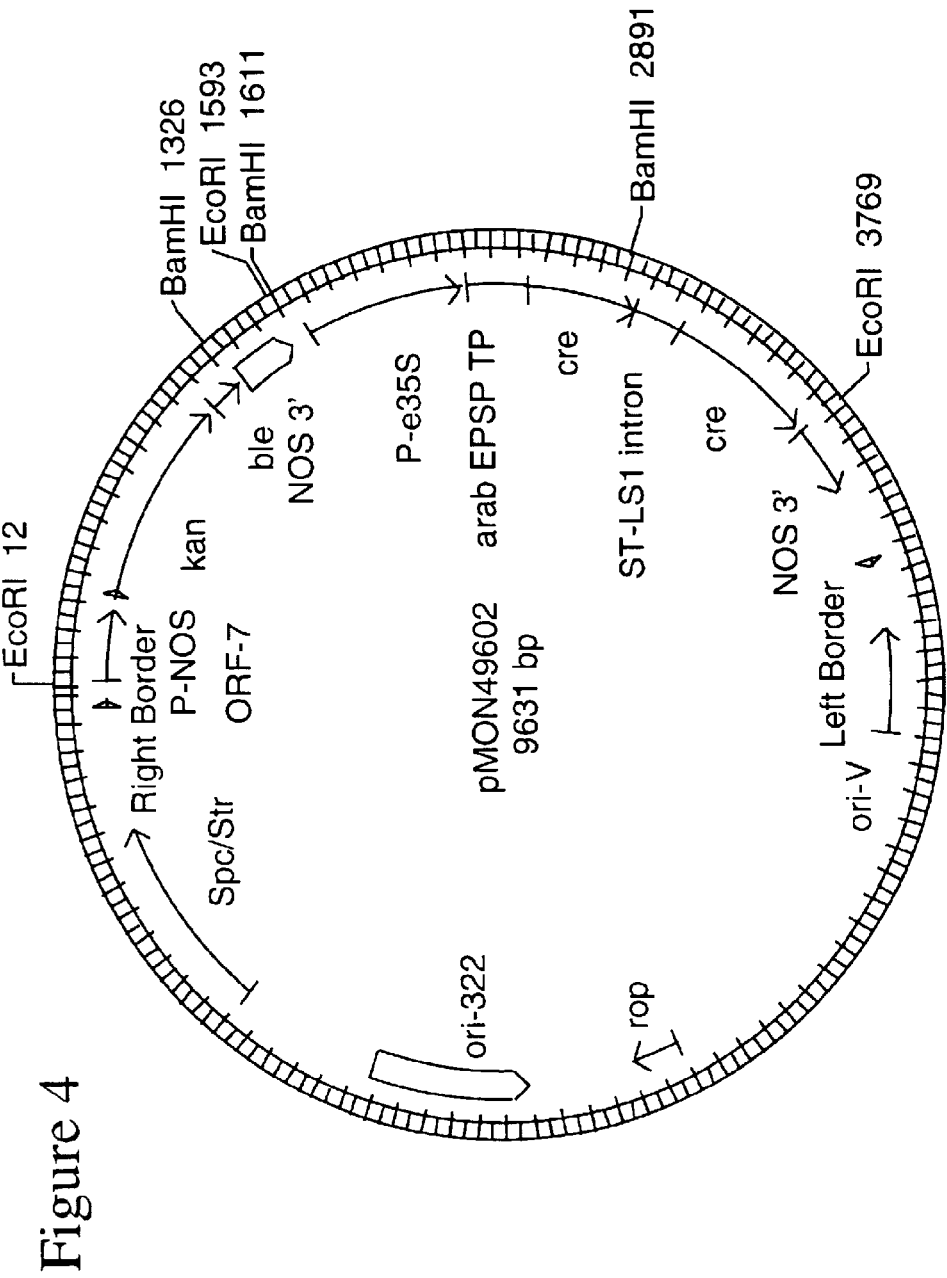
FIG. 4 provides a schematic diagram of the nuclear construct pMON49602.

The construct pMON49602 (FIG. 4) is a double border plant transformation vector containing the Cauliflower Mosaic Virus 35S promoter (CaMV 35S), a chloroplast transit peptide (CTP) from the *Arabidopsis thaliana* EPSP synthase gene (Klee et al., 1987, Mol Gen Genet 210:437–442), a nucleic acid sequence encoding the bacteriophage P1 Cre recombinase, nopaline synthase transcriptional termination sequence, as well as the kanamycin resistance gene under the regulatory control of the nopaline synthase promoter and transcriptional termination region.

Figure 5:
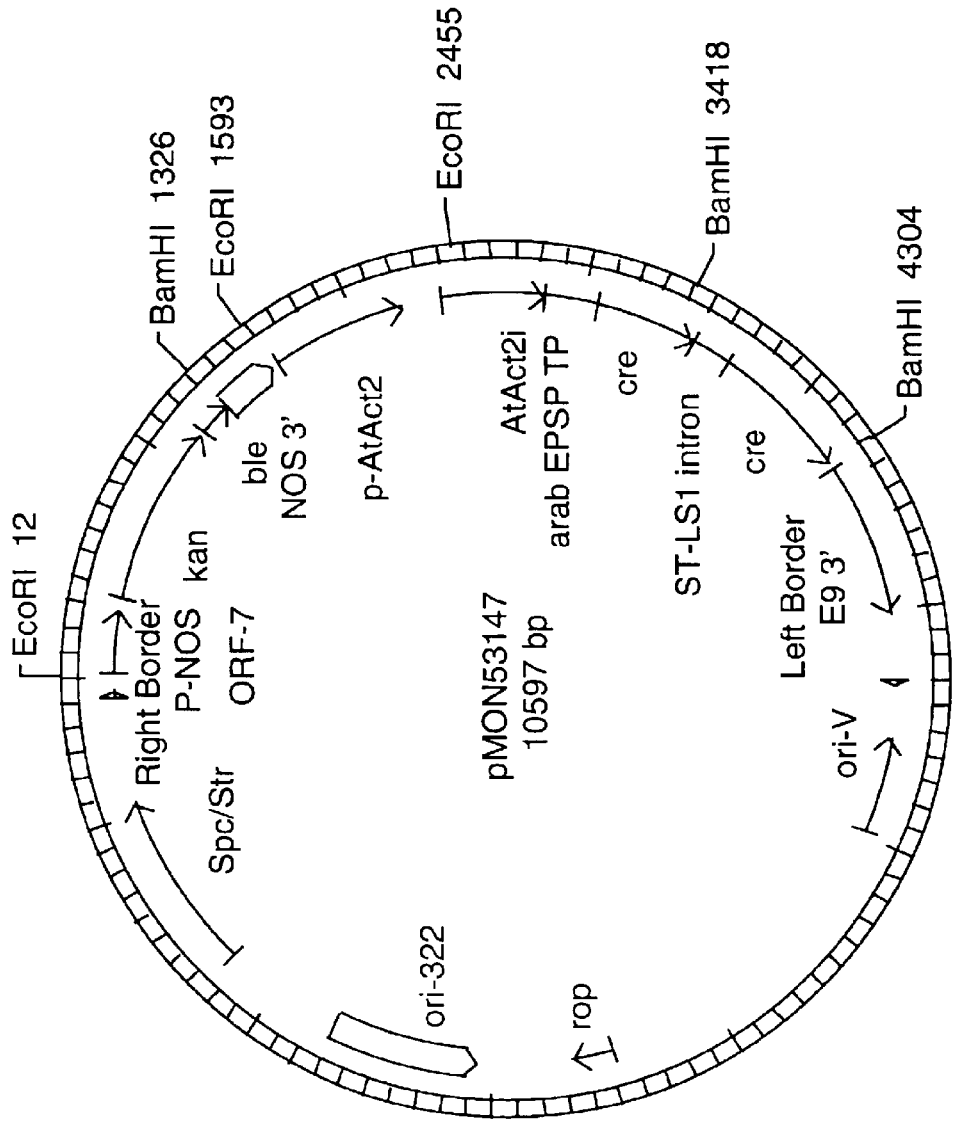
FIG. 5 provides a schematic diagram of the nuclear construct pMON53147.

The construct pMON53147 (FIG. 5) is a double border plant transformation construct containing the *Arabidopsis* Actin2 promoter and intron (An et al. (1996) *Plant J* 10(1):107–21) controlling the expression of the CTP-Cre recombinase fusion, and nopaline synthase transcriptional termination sequence, as well as the kanamycin resistance gene under the regulatory control of the CaMV 35S promoter and nopaline synthase transcriptional termination region.

Figure 6:
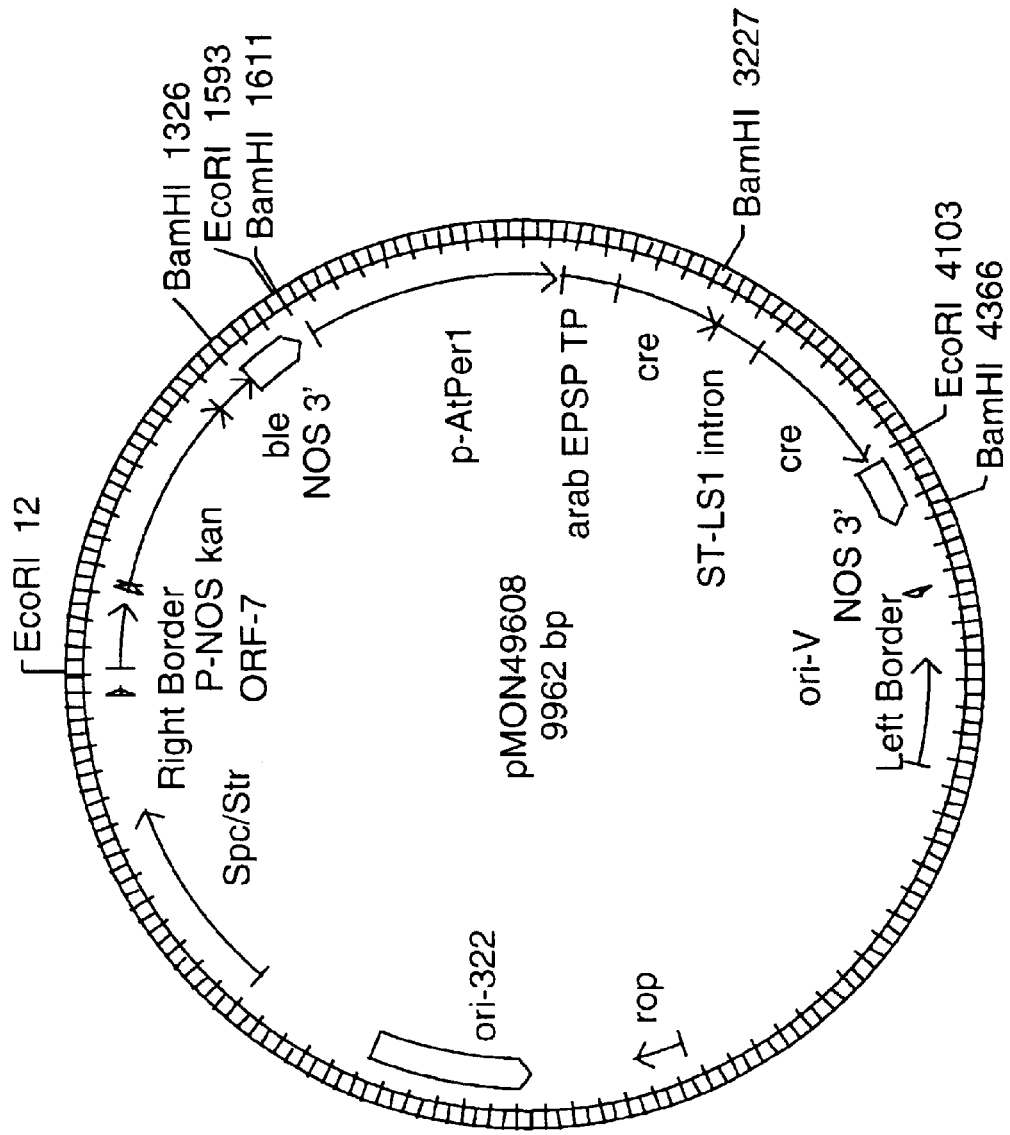
FIG. 6 provides a schematic diagram of the nuclear construct pMON49608.

The construct pMON49608 (FIG. 6) is a double border plant transformation construct containing the *Arabidopsis* Perl promoter (Haslekas et al. (1998) *Plant Mol Biol* 36(6):833–45) for expression of the CTP-Cre recombinase fusion, and the nopaline synthase transcriptional termination region, as well as the kanamycin resistance gene under the regulatory control of the CaMV 35S promoter and nopaline synthase transcriptional termination region.

The Cre recombinase sequence employed in all of the above constructs contains an intron sequence from the potato ST-LS1 gene (Vancanneyt et al., 1990, *Mol Gen Genet* 220:245–250) to prevent possible complications as a result of expression of the Cre protein in bacterial cells during cloning and manipulations.

Example 2

Plant Transformation

2A. Nuclear Transformation

Tobacco plants transformed to express the constructs pMON49602, pMON53147 and pMON49608 in the nucleus of a plant cell may be obtained as described by Horsch et al. (*Science* (1985) 227:1229–1232).

2B. Plastid Transformation

Tobacco plastids are transformed by particle gun delivery of microprojectiles as described by Svab and Maliga (*Proc. Natl. Acad. Sci.* (1993) 90:913–917), and described herein.

Dark green, round leaves are cut, preferably from the middle of the shoots, from 3–6-week-old *Nicotiana tabacum* cv. Havana that have been maintained in vitro on hormone-free MS medium (Murashige and Skoog (1962) *Physiol Plant.* 15,473–497) supplemented with B5 vitamins in Phytatrays or sundae cups with a 16-hour photoperiod at 24° C. Each cut leaf is then placed adaxial side up on sterile filter paper over tobacco shoot regeneration medium (TSO medium: MS salts, 1 mg/L $N^6$-benzyladenine, 0.1 mg/L 1-naphthaleneacetic acid, 1 mg/L thiamine, 100 mg/L inositol, 7 g/L agar pH 5.8 and 30 g/L sucrose). Leaves are preferably placed in the center of the plate with as much contact with the medium as possible. The plates are preferably prepared immediately prior to use, but they may be prepared up to a day before transformation by particle bombardment by wrapping in plastic bags and storing at 24° C. overnight.

Tungsten or gold particles are sterilized for use as microcarriers in bombardment experiments. Particles (50 mg) are sterilized with 1 mL of 100% ethanol and stored at −20° C. or −80° C. Immediately prior to use, particles are sedimented by centrifugation, washed with 2 to 3 washes of 1 mL sterile deionized distilled water, vortexed and centrifuged between each wash. Washed particles are resuspended in 500 µL 50% glycerol.

Sterilized particles are coated with DNA for transformation. Twenty-five microliter aliquots of sterilized particles are added to a 1.5-mL microfuge tube, and 5 µg of DNA of interest is added and mixed by tapping. Thirty-five microliters of a freshly prepared solution of 1.8M $CaCl_2$ and 30 mM spermidine is added to the particle/DNA mixture, mixed gently, and incubated at room temperature for 20 minutes. The coated particles are sedimented by centrifuging briefly. The particles are washed twice by adding 200 µL 70% ethanol, mixing gently, and centrifuging briefly. The coated particles are resuspended in 50 µL of 100% ethanol and mixed gently. Five to ten microliters of coated particles are used for each bombardment.

Transformation by particle bombardment is carried out using the PDS 1000 Helium gun (Bio Rad, Richmond, Calif.) using a modified protocol described by the manufacturer.

Plates containing the leaf samples are placed on the second shelf from the bottom of the vacuum chamber and bombarded using the 1100 p.s.i. rupture disk. After bombardment, petri plates containing the leaf samples are wrapped in plastic bags and incubated at 24° C. for 48 hours.

After incubation, bombarded leaves are cut into approximately 0.5 $cm^2$ pieces and placed abaxial side up on TSO medium supplemented with 500 µg/mL spectinomycin. After 3 to 4 weeks on the selection medium, small, green spectinomycin resistant shoots will appear on the leaf tissue. These shoots will continue to grow on spectinomycin containing medium and are referred to as primary putative transformants.

When the primary putative transformants have developed two to three leaves, two small pieces (approximately 0.5 $cm^2$) are cut from each leaf and used for either selection or for a second round of shoot regeneration. One piece is placed abaxial side up on plates containing TSO medium supplemented with 500 µg/1 mL spectinomycin, and the other piece is placed abaxial side up on TSO medium supplemented with 500 µg/mL each of spectinomycin and streptomycin. Positive transformants are identified as the shoots that form green callus on the TSO medium containing spectinomycin and streptomycin.

After 3 to 4 weeks, the tissue placed on TSO medium containing only spectinomycin, which has been identified as positive on the TSO medium with spectinomycin and streptomycin, will develop green shoots. Two to four shoots of each positive transformant are selected and transferred to TSO medium supplemented with 500 µg/mL spectinomycin for generation of roots. Southern analysis is performed on two shoots to confirm homoplasmy as described below. Shoots from homoplasmic events are transferred to the greenhouse for seed production, whereas transformants that are not homoplasmic are sent through a second round of regeneration on TSO medium with 500 µg/mL spectinomycin to attain homoplasmy.

Example 3

In vivo Excision of the aadA Marker Gene

For the excision of the aadA marker gene expression cassette flanked by the loxP sites, a variety of methods can be employed. One method involves the use of homoplasmic pMON53117 and pMON53119 transformants in retransformation experiments with the nuclear recombinase constructs.

For example, homoplasmic plastid transformants derived from plastid vector pMON53119 (Nt-53119 lines) carrying the disrupted GFP gene can be used as recipient for retransformation. The nuclear re-transformation vector pMON49602 carrying the constitutive 35S::CTP-Cre recombinase gene can be introduced via *Agrobacterium*-mediated nuclear transformation and selection for kanamycin resistance encoded in the transformation vector. The CTP provides for the localization of the Cre gene product into the plastids for excision of the aadA gene cassette. Transformed lines that have excised the plastid aadA gene can be identified by kanamycin resistance and GFP fluorescence and spectinomycin and/or streptomycin susceptibility.

In this example, excision of aadA can occur from all of the recipient's Nt-53119 plastid genomes or only a fraction of these. Therefore, GFP fluorescence can be observed either completely throughout the newly regenerating plantlet or only in sectors of the regenerant. Shoots that show complete or nearly complete GFP fluorescence can be analyzed further and grown to maturity.

The nuclear CTP-Cre and selectable marker genes can also be removed from the re-transformed Nt-53119 plants by genetic segregation in T1 seedlings. Pollen from wild-type plants can be used to pollinate the nuclear re-transformed Nt-53119 plants. Because the nuclear re-transformed lines are hemizygous, the seedlings generated from the back-cross segregate the nuclear transgenes in a 2 (wild-type):2 (transgene +) ratio. Because the re-transformed Nt-53119 plant is used as maternal parent, all of the progeny will have the plastid transgene of interest. Therefore, the final result is ½ of the progeny that carry the plastid GFP gene without the plastid aadA selectable marker and also do not carry any nuclear transgenes.

Loss of the nuclear transgenes can be monitored by germinating seeds on medium containing kanamycin monosulfate (100 mg/L). The seedlings that completely bleach on kanamycin have segregated out the nuclear nptll selectable marker and the CTP-Cre genes. Bleached seedlings can be rescued onto drug-free medium and screened for spectinomycin sensitivity and GFP fluorescence. Southern analysis can be performed to confirm the final GFP+, aadA−, nptll− transgenic plants.

Another method for the in vivo excision of the aadA expression cassette involves the crossing of plastid transformed lines to nuclear transformed CTP-Cre recombinase lines.

Nuclear transformants carrying CTP-Cre recombinase genes can be generated via *Agrobacterium*-mediated transformation using kanamycin selection encoded on the nuclear transformation vector. Independent lines for each of the different CTP-Cre constructs (35S::CTP-Cre, Act2::CTP-Cre, Perl::CTP-Cre) can be generated. These lines are characterized to identify single copy inserts to be used in subsequent crosses to the plastid transformed lines. Each of these nuclear transformed lines is hemizygous for the nuclear transgenes.

For example, homoplasmic plastid transformants, obtained from vectors pMON53117 and pMON53119, can be cross pollinated with the hemizygous nuclear CTP-Cre lines. Alternatively, transplastomic lines containing pMON53117 and pMON53119 can be used in transformation to obtain lines having both a plastid construct and a recombinase construct. The nuclear transformed lines are used as pollen donor; the plastid transformed lines are used as maternal recipient. CTP-Cre gene product is imported into plastids for excision of the aadA gene. This excision can occur during zygote formation (before seeds germinate) or subsequent seedling germination, depending on the activity of the promoter used to drive the nuclear CTP-Cre gene. The Act2 and Perl promoters are reported to be active during fertilization, therefore excision occurs early in development. The 35S promoter is constitutive and active during seedling development.

Early expression of the CTP-Cre and excision during zygote formation of the sequence flanked by the loxP allows deletion of the aadA gene in all or most of the plastid genome copies. Furthermore, because the nuclear transformed lines are hemizygous, a 2 (wild-type) to 2 (nuclear transgene +) segregation can occur in the seedlings. Seeds can be germinated on medium containing kanamycin monosulfate (100 mg/L) to identify wild-type nuclear background. Tissues that bleach on kanamycin will then be screened for spectinomycin sensitivity (aadA excision) and GFP expression. Transformants derived from pMON53117 will be uniformly GFP positive, whereas transformants derived from pMON53119 will only be GFP positive if the aadA gene is excised from at least one chloroplast genome. Southern analysis will be performed to confirm transgenic plants.

If excision occurs later in the development of seedlings, the deletion of the aadA gene will occur in only a partial population of the plastid genome copies. These will be identified as F1 plants that express both spectinomycin resistance and GFP. In this case, kanamycin-sensitive, GFP+ lines will be grown to maturity again and allowed to set self seed. Homoplasmic plants that no longer carry any aadA gene copies can be identified in the subsequent next generation.

Example 4 aadA Disrupting GFP; Nuclear Retransformation

Line Nt-53119 was generated from plastid transformation of wild-type tobacco with plasmid pMON53119 using standard microprojectile bombardment protocols and spectinomycin selection as described in Example 2. Primary plastid transformed Nt-53119 lines were verified by Southern blot analysis and were initially heteroplasmic. Plants were regenerated from leaf samples of the primary transformed Nt-53119 line until homoplasmic plants were identified. The homoplasmic plastid-transformed Nt-53119 lines carry the inactive GFP gene due to disruption by aadA (flanked by lox sites). Under fluorescent microscopy, these lines appear red due to chlorophyll autofluorescence. Homoplasmic Nt-53119 lines were subsequently used for nuclear retransformations by *Agrobacterium*.

*Agrobacterium* nuclear retransformation of Nt-53119 plastid lines was performed according to standard procedures. Two different binary vectors were used for the retransformations: Plasmid pMON49602 and pMON53147 carrying the CTP-Cre gene driven by the CaMV 35S and the *Arabidopsis thaliana* Act2 promoters, respectively. These binary vectors also carry the nptll gene encoding resistance to kanamycin used as the selectable marker for the retransformations.

Kanamycin-resistant nuclear retransformed lines were screened by visual observation for GFP fluorescence, which indicates excision of the aadA gene from the disrupted GFP gene, thus re-activating GFP function. After *Agrobacterium* transformation of the Nt-53119 line, numerous GFP positive shoots were observed from transformations with binary vectors carrying CTP-Cre driven by either the CaMV 35S or the Act2 promoter. These data indicate that CTP-Cre can be properly targeted to plastids and marker excision can occur early during shoot development.

GFP+shoots from multiple independently retransformed lines were isolated and moved to individual tissue culture plates for continued growth. The independent nuclear retransformed shoots were assayed for the presence of the plastid transgenes aadA and GFP by Southern blot analysis. Leaf pieces from young shoots were dissected, and total cellular DNA was prepared. Total cellular DNA was digested with BamHI and probed with plastid DNA flanking the transgene insertion site. By this analysis, the size of the insertion in the plastid genome can be determined and therefore the presence of the GFP gene and absence of aadA can be molecularly visualized.

Multiple representative nuclear retransformed Nt-53119 lines derived from *Agrobacterium* transformation with the pMON53147 binary vector carrying the Act2-promoter driving CTP-Cre were analyzed by Southern blots using plastid DNA flanking the insertion site as probe. These lines are referred to as Nt-Act2-53119- followed by the clone number. Although the wild-type untransformed tobacco control has a hybridizing band at the predicted 3.27 kb size, the parental Nt-53119 plastid line prior to nuclear retransformation has a single hybridization signal at the size expected for the integrated aadA and GFP genes (unexcised; 5.58 kb). All Nt-Act2-53119- lines (for example, lines Nt-Act2-53119-4, 9, 11, 12, 14, 16, 20, 23, 25, 38, 40, and 43) carry a strong hybridizing band at the size of 4.34 kb as expected for the excision of the aadA gene. When the blot is stripped and reprobed with the aadA coding region, there is no hybridization signal to nearly all of the nuclear retransformed lines. This result shows that these lines have completely lost the aadA gene from all of the plastid genomes, indicating that CTP-Cre activity is efficient for removal of genes from the multiple plastid genomes per cell. Only one exception is seen in line Nt-Act2-53119-43, which still carries some aadA-containing plastid genomes, as evidenced by a higher parental molecular weight band and a corresponding band when probed with aadA.

A few of the Nt-Act2-53119- lines carried an additional one or two hybridizing bands that may represent alternate aadA excision events from the plastid genome. One band was interemediate in size between the size predicted for the wild-type fragment and the correctly excised fragment, whereas the other band was smaller in size than the predicted wild-type size. To investigate these events further, subclones of these nuclear retransformed lines were generated by a new round of plant regeneration. Multiple subclones of each line were analyzed for segregation to homoplasmy of the putative alternate excision events. Representative subclones were analyzed by Southern blot hybridization. The two different classes of putative alternate excision events could be purified to homoplasmy in subclones. For example, Nt-Act2-53119-38A,B,C and Nt-Act2-53119-40C carry the intermediate-sized band in a homoplasmic form. The Nt-Act2-53119-14B,C lines carry the smaller-sized band in a homoplasmic form. In contrast, the original Nt-Act2-53119-27 line that carried exclusively the correct excision event still carries only the correct excision event in its subclones (Nt-Act2-53119-27A,B,C). This latter result suggests that alternate excision events occurred early during development of the nuclear retransformed lines, which are then stable and no longer undergo alternate excision events during normal growth.

Multiple representative nuclear retransformed Nt-53119 lines after *Agrobacterium* transformation with the pMON49602 binary vector carrying the 35S-promoter driving CTP-Cre were also analyzed by Southern blots. Results are analogous to those observed with the pMON53147 binary vector. The retransformed lines are referred to as Nt-35S53119- line number. Nearly all of the nuclear retransformed lines analyzed (for example, Nt-35S-53119-9, 10, 11, 12, 14, and 18) carried the correct sized 4.34 kb excised band when probed with the flanking region probe. Re-probing with the aadA coding region confirmed the absence of the aadA gene in all of these lines. In addition to the correct excision band, lines Nt-35S-53119-10, Nt-35S-53119-11 and Nt-35S-53119-18 also carried the alternate excision band(s). Interestingly, line Nt-35S- 53119-2 carried only the smaller alternate excision band and no precise 4.34 kb excision band.

Subclones of the Nt-35S-53119 lines were generated and analyzed to determine if the alternate excision events could be purified to homoplasmy. The Nt-35S-53119-10A subclone carried predominantly the intermediate-sized excision event, whereas the Nt-35S-53119-10B,C and Nt-35S-53119-2A,B,C subclones carried the smaller alternate excision band in a homoplasmic form. In contrast, the Nt-35S-53119-11 line that carried both correct excision and alternate excision bands now carries exclusively the correct excision band in its subclones, Nt-35S-53119-11A,B,C. This latter result indicates that the correct excision event can be purified to homoplasmy even if the original transformant carried alternate excision events.

The above results indicate that CTP-Cre is capable of efficient excision of genes from the multiple plastid genomes per cell after nuclear retransformation into established plastid transformed lines. Excision is efficient when the CTP-Cre gene is driven by a constitutive promoter (35S) or the meristem-specific promoter (Act2). Although alternate excision events can also occur in both cases, these are relatively infrequent compared to correct excision events and apparently only occur early in development of the nuclear transformed line. Furthermore, the alternate excision events can be purified to homoplasmy if desired, in subclones of the original nuclear retransformed lines. Likewise, the correct excision events can be purified to homoplasmy in cases where the original transformant had a mix of correct and alternate excision events.

Molecular characterization of alternate excision events:

PCR was used to isolate DNA fragments spanning the alternate excision sites for both the intermediate and smaller sized bands. PCR primers that flank the insertion site of the foreign genes in Nt-53119 lines were used: one primer in the coding region of the 16SrRNA gene (SEQ ID NO:2) and the other primer near to the rps7/3'-rps12 coding region (SEQ ID NO:3). Plant lines Nt-Act2-53119-38 and Nt-35S-53119-2 were used to isolate the alternate excisions. The PCR fragments were cloned into a pUC vector and DNA was subsequently prepared for sequencing the alternate excision events.

Figure 7:
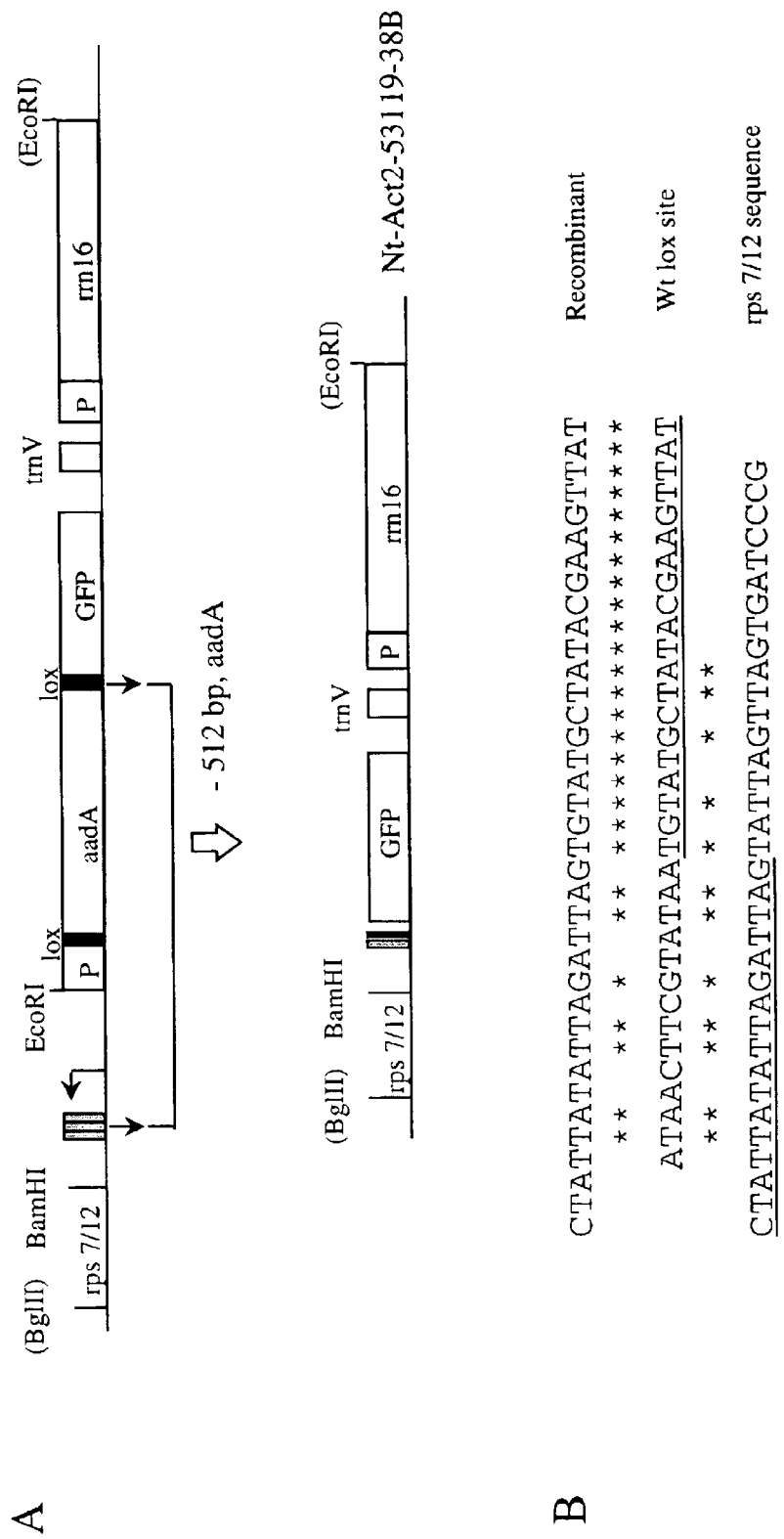
FIG. 7 shows an alternate excision in clone Nt-Act2-53119-38.

FIG. 7 shows the results of the PCR and sequencing analysis of line Nt-Act2-53119-38. The intermediate-sized excision event apparently occurred through recombination of one lox site flanking the aadA gene and an alternate site (SEQ ID NO:4) in the plastid genome. The alternate site resides downstream of the promoter of the rps7/3'-rps12 gene, 512 nucleotides from the transgene insertion site. The alternate excision event therefore deleted the aadA gene plus 512 bp of the resident plastid genome, resulting in a transplastomic genome carrying the transgenic GFP gene without its promoter. Note that deletion of the 512 nt of resident plastid DNA apparently has no phenotypic consequence, as homoplasmic plants regenerated from this line show no aberrant phenotype. The sequence of the recombinant junction (SEQ ID NO:5) is shown in FIG. 7b.

Figure 8:
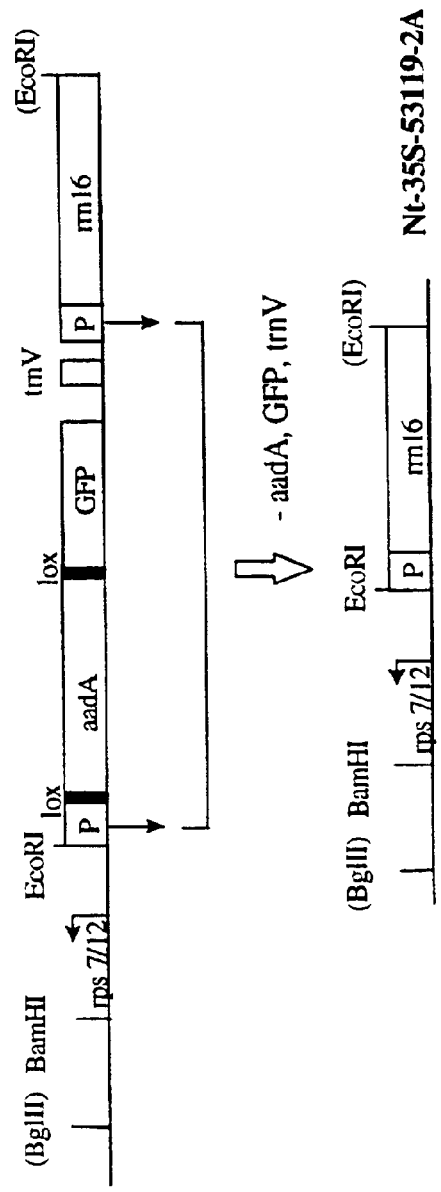
FIG. 8 shows an alternate excision in clone Nt-35S-53119-2.

FIG. 8 shows the results of the PCR and sequencing analysis of line Nt-35S-53119-2. The smaller-sized alternate excision event apparently occurred through recombination between the identical, repeated Prrn sequences; one Prrn driving expression of the GFP transgene and the other Prrn driving the expression of the endogenous 16SrRNA gene. The direct repeat orientation of these two Prrn sequences caused a deletion of the intervening transgenic aadA and GFP genes as well as the endogenous plastid trn V gene. The resultant plastid genome therefore does not carry any transgenes and is deficient for the endogenous trn V gene normally located in this region of the genome. Interestingly, there is no apparent phenotypic consequence of trn V gene. At this time, we do not know why alternate excision through the directly repeated Prrn sequences occurred. We speculate that the close proximity of the lox sites and Cre protein stimulated homologous recombination between the directly repeated Prrn sequences in that local region of the plastid genome.

Example 5

Maternal Inheritance of the Plastid GFP Transgene and Mendelian Segregation of the Nuclear-encoded Transgenes.

For utility in biotechnology applications, it is desirable to remove the nuclear-encoded transgenes (nptll and CTP-Cre) from seed progeny by segregation. To this end, primary transformed lines and subclones from Nt-Act2-53119 and Nt-35S-53119 lines were grown to maturity in the greenhouse and allowed to self-pollinate. Because plastids are maternally inherited, the plastid-encoded GFP transgene should be present in all seed progeny of self pollination. On the other hand, the nuclear-encoded transgenes should segregate according Mendelian ratios and therefore be present only in a subset of the seed progeny.

To test inheritance and segregation of the transgenes, self seed was germinated on three different medias, all based on TSO media. Spectinomycin media (500 µg/mL) was used to detect if any plastid-encoded aadA gene remained after excision. Kanamycin media (100 µg/mL) tested for the presence of the nuclear-encoded nptII gene. Media without antibiotic was used as control.

As an example of this analysis, seedlings from line Nt-Act2-53119-12 are described. A Southern blot analysis was performed on randomly chosen seedlings picked from germination medium without antibiotic. All of these seedlings show the hybridization pattern expected from complete excision of the aadA gene and subsequent maternal inheritance of the plastid-encoded GFP in a homoplasmic state. As expected, seeds from this line were uniformly sensitive to spectinomycin, confirming complete loss of the aadA gene.

Seeds from the Nt-Act2-53119-12 line were also sown on medium containing kanamycin to test for the nuclear-encoded nptII gene. As expected for a Mendelian inherited trait, ~50% of the selfed seed progeny were sensitive (bleached) to kanamycin. This analysis indicates that we have succeeded in generating plastid-transformed lines that do not carry the nuclear-encoded transgenes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for performing multiple rounds of plastid transformations in a plant cell plastid using the same selectable marker for selection of transplastomic plants comprising:
   (a) introducing into a plant cell a first recombinant DNA sequence comprising a construct capable of being integrated into the plastid genome of the plant cell, said construct comprising an expression cassette comprising a DNA sequence of interest to be expressed in the plastid and a selectable marker cassette comprising a promoter that initiates expression of an operably linked DNA sequence in a plant plastid, a DNA sequence encoding a protein that permits for the selection of a transformed plastid and a 3' transcription termination region, said selectable marker cassette flanked by a pair of compatible recombining sites arranged in parallel orientation as direct repeats, to produce a plant cell having a plastid containing said first recombinant DNA sequence;
   (b) selecting for the cell containing a transformed plastid;
   (c) providing a recombinase compatible to said pair of compatible recombining sites to said plant cell to permit excision of said DNA sequence encoding a protein that permits for the selection of a transformed plastid and producing excision of said DNA sequence;
   (d) regenerating a transplastomic plant containing said first recombinant DNA sequence without said DNA sequence encoding a protein that permits for the selection of a transformed plastid from said plant cell;
   (e) introducing into a plant cell of said transplastomic plant a second recombinant DNA sequence comprising a construct capable of being integrated into the plastid genome of the plant cell, said construct comprising a second expression cassette comprising a second DNA sequence of interest to be expressed in said plastid and a second selectable marker cassette comprising a promoter that initiates expression of an operably linked DNA sequence in a plant plastid, a DNA sequence encoding the same protein as in the first recombinant DNA sequence that permits for the selection of a transformed plastid and a 3' transcription termination region, into a plant cell of said transplastomic plant obtained from said regenerated plant thereby producing a plastid having said second recombinant DNA sequence in said plant cell of said transplastomic plant; and
   (f) producing a transplastomic plant having said first and second recombinant DNA sequences introduced sequentially into said plastid using the same selectable marker for the second recombinant DNA sequence as used for the selection of the first recombinant DNA sequence.

2. The method according to claim 1, wherein said recombinase is provided to said plant cell by introducing a third recombinant DNA sequence comprising in an operably coupled 5' to 3' manner:
   a transcriptional initiation region, a plastid targeting region, and a nucleic acid sequence encoding recombinase.

3. The method according to claim 1, wherein said DNA sequence of interest in said first or second expression cassette provides for herbicide resistance to said plant cell.

4. The method according to claim 1, wherein said pair of compatible recombining sites is selected from the group consisting of Lox, FRT and R.

* * * * *

UNITED STATES PATENT AND TRADEMARK OFFICE
CERTIFICATE OF CORRECTION

| | | |
|---|---|---|
| PATENT NO. | : 6,849,778 B1 | Page 1 of 1 |
| APPLICATION NO. | : 09/688851 | |
| DATED | : February 1, 2005 | |
| INVENTOR(S) | : Jeffrey M. Staub, Peter H.J. Hajdukiewicz and Larry Gilbertson | |

It is certified that error appears in the above-identified patent and that said Letters Patent is hereby corrected as shown below:

On Title Page, in field (75), replace "Peter H. J. Hajdukiewicz" with -- Peter T. J. Hajdukiewicz --.

Signed and Sealed this

Fifth Day of June, 2007

JON W. DUDAS
*Director of the United States Patent and Trademark Office*